(12) United States Patent
Krasts et al.

(10) Patent No.: US 12,357,304 B2
(45) Date of Patent: Jul. 15, 2025

(54) MATERIAL COMBINATIONS AND PROCESSING METHODS FOR A SURGICAL INSTRUMENT

(71) Applicant: Applied Medical Resources Corporation, Rancho Santa Margarita, CA (US)

(72) Inventors: Andrew Krasts, San Clemente, CA (US); Darci Darnall, Rancho Santa Margarita, CA (US); Eric J. Weiss, San Clemente, CA (US); Timothy M. Hopkins, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 18/756,597

(22) Filed: Jun. 27, 2024

(65) Prior Publication Data

US 2024/0341759 A1 Oct. 17, 2024

Related U.S. Application Data

(63) Continuation of application No. 17/514,180, filed on Oct. 29, 2021, now Pat. No. 12,048,431.

(Continued)

(51) Int. Cl.
*A61B 17/072* (2006.01)
*A61B 17/00* (2006.01)

(52) U.S. Cl.
CPC .. *A61B 17/072* (2013.01); *A61B 2017/00526* (2013.01); *A61B 2017/00836* (2013.01);
(Continued)

(58) Field of Classification Search
CPC ........ A61B 17/072; A61B 2017/00526; A61B 2017/00836; A61B 2017/00845;
(Continued)

(56) References Cited

U.S. PATENT DOCUMENTS 2,073,960 A  3/1937 Crosby
2,140,593 A  12/1938 Pankonin
(Continued)

FOREIGN PATENT DOCUMENTS

EP  0 251 444 A1  1/1988
EP  0 492 283 A1  7/1992
(Continued)

OTHER PUBLICATIONS

European Patent Office, European Search Report for European Application No. 07784007.2, entitled "Surgical Stapler," dated Jun. 15, 2012, 6 pgs.
(Continued)

*Primary Examiner* — Veronica Martin
(74) *Attorney, Agent, or Firm* — John F. Heal

(57) ABSTRACT

Surface preparation for sliding surfaces can enhance wear performance for surgical instruments such as surgical staplers which include reusable mechanisms that are used multiple times with single use reload cartridges. To reduce the potential for galling wear in a metal-to-metal sliding engagement, a combination of surface hardening, surface finish, and surface coatings can be applied to metallic components of a surgical instrument. Surface hardening techniques can allow further manufacturing operations such as welding without compromising the strength of the underlying metal substrate. With stainless steel metal substrates, as surface or case hardening techniques can reduce corrosion resistance, a surface coating can be applied to inhibit surface oxidation as well as provide a barrier to metal-to-metal (Continued)

contact. A further lubricious coating layer such as a bone wax coating layer can enhance galling resistance.

13 Claims, 10 Drawing Sheets

Related U.S. Application Data

(60) Provisional application No. 63/107,321, filed on Oct. 29, 2020.

(52) U.S. Cl.
CPC ............ *A61B 2017/00845* (2013.01); *A61B 2017/00933* (2013.01)

(58) Field of Classification Search
CPC .... A61B 2017/00933; A61B 17/07207; A61B 2017/07285; A61B 17/068; A61B 17/2909; A61B 2017/07264; A61B 2017/07278; A61B 2017/2923; A61B 2017/2927; A61B 2017/2946
See application file for complete search history.

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,180,092 A | 1/1993 | Crainich |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,115 A | 11/1996 | Nicholas |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |

(56) References Cited

U.S. PATENT DOCUMENTS

| | | |
|---|---|---|
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |

(56) References Cited

U.S. PATENT DOCUMENTS

| | | |
|---|---|---|
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |

(56) References Cited

U.S. PATENT DOCUMENTS

| | | |
|---|---|---|
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |

(56) References Cited

U.S. PATENT DOCUMENTS

| | | |
|---|---|---|
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0143806 A1 | 6/2009 | Witt et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Laurent et al. |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0109186 A1 | 5/2012 | Parrott et al. |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0253298 A1 | 10/2012 | Henderson et al. |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1* | 1/2014 | Onukuri ............... C10M 111/04 227/177.1 |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |

(56) References Cited

U.S. PATENT DOCUMENTS

| | | |
|---|---|---|
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2015/0380187 A1 | 12/2015 | Zergieebel et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |
| 2019/0261984 A1 | 8/2019 | Nelson et al. |
| 2020/0268381 A1 | 8/2020 | Roberts et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 044 893 A2 | 9/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 815 705 A1 | 12/2014 |
| EP | 2 923 661 A2 | 3/2015 |
| EP | 2 853 204 A1 | 4/2015 |
| EP | 2 891 462 A1 | 7/2015 |
| EP | 2 926 742 A1 | 10/2015 |
| EP | 2 942 020 A2 | 11/2015 |
| EP | 2 959 851 A1 | 12/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |

(56) References Cited

FOREIGN PATENT DOCUMENTS

| WO | WO 02/096327 A2 | 12/2002 |
|---|---|---|
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |
| WO | WO 2020/077531 A1 | 4/2020 |

OTHER PUBLICATIONS

Ethicon Endo Surgery, Inc., Contour Curved Cutter Stapler, 2014, 2 pgs.
Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," mailed Aug. 5, 2014, 14 pgs.
European Patent Office, International Search Report and Written Opinion for International Application No. PCT/US2014/028211, entitled "Surgical Stapler with Partial Pockets," mailed Sep. 8, 2014, 17 pgs.
International Searching Authority, U.S., The International Search Report and the Written Opinion of the International Searching authority for international application PCT/US2014/027768, titled "Surgical Stapler with Expandable Jaw", mailed Jul. 25, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", mailed Sep. 15, 2015, 22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentabilityfor International Application No. PCT/US2015/035379, entitled "Surgical Stapler with Circumferential Firing," dated Dec. 22, 2016, 14 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," mailed Sep. 12, 2017, 22 pgs.
European Patent Office, The International Search Report and the Written Opinion of the International Searching Authority for International Application No. PCT/US2017/027213, entitled "Surgical Stapler Having a Powered Handle," mailed Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," mailed Sep. 14, 2017, 21 pgs.
European Patent Office, The International Search Report and Written Opinion of the International Searching Authority for International Application No. PCT/US2016/045993 titled "Surgical Stapler Having Locking Articulation Joint", mailed Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," mailed Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, The International Search Report and the Written Opinion of the International Searching Authority for International Application No. PCT/US2020/019938, entitled "Surgical Stapling Instrument Having a Two-Position Mechanism," mailed Jun. 18, 2020, 16 pgs.
European Patent Office, Extended European Search Report for European Application No. EP 20157713.7, entitled "Surgical Stapler with Expandable Jaw," dated May 11, 2020, 6 pgs.
European Patent Office, Extended European Search Report for European Application No. EP 20161294.2, entitled "Surgical Stapler with Self-Adjusting Staple Height," dated Jun. 22, 2020, 6 pgs.
European Patent Office, Extended European Search Report for European Application No. EP 20197859.0, entitled "Surgical Stapler with Circumferential Firing," dated Jan. 28, 2021, 13 pgs.

(56) References Cited

OTHER PUBLICATIONS

International Searching Authority/ EPO, Invitation to Pay Additional Fees for PCTUS2020/025496, entitled "Reload Cover for Surgical Stapling System," dated Jun. 18, 2019, 15 pgs.
European Patent Office, The International Search Report and the Written Opinion of the International Searching Authority for International Application No. PCT/US2020/025496, entitled "Reload Cover for Surgical Stapling System," mailed Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
European Patent Office, The International Search Report and Written Opinion for International Application No. PCT/US2020/067540, mailed May 3, 2021, entitled "Electrosurgical System with Tissue and Maximum Current Identification," 12 pages.
The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.
"Carpenter's Stainless Steel Blue Book Selection/Alloy Data/Fabrication," www.carpentertechnology.com, 2021, 87 pgs.
Hummel, et al., "Threshold galling load and frictional behavior of stainless steel couples in line contact," Science Direct (Abstract), Aug.-Sep. 2003, pp. 504-508, vol. 255, Issues 1-6.
European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" mailed Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" mailed Feb. 11, 2022, 15 pgs.
European Patent Office, The International Search Report and the Written Opinion of the International Searching Authority for International Application No. PCT/US2021/057365, entitled "Surgical Stapler Having a Powered Handle" mailed Apr. 13, 2022, 21 pgs.
European Patent Office, The International Search Report and the Written Opinion of the International Searching Authority for International Application No. PCT/US2022/012452, entitled "Surgical Stapler Having Shaft Recognition Mechanism" mailed Apr. 13, 2022, 13 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203464.7, entitled "Surgical Stapler with Partial Pockets," dated Dec. 20, 2022, 9 pgs.
European Patent Office, Extended European Search Report for European Application No. EP 22203599.0, entitled "Surgical Stapler Having a Powered Handle," dated Feb. 7, 2023, 7 pgs.
The International Bureau of WIPO, International Preliminary Report on Patentability, for International Application No. PCT/US2021/057231, entitled "Material Combinations and Processing Methods for a Surgical Instrument," dated May 11, 2023, 10 pgs.
The International Bureau of WIPO, International Preliminary Report on Patentability, for International Application No. PCT/US2021/057278, entitled "Actuation Shaft Retention Mechanism for Surgical Stapler," dated May 11, 2023, 10 pgs.
The International Bureau of WIPO, International Preliminary Report on Patentability, for International Application No. PCT/US2021/057365, entitled "Surgical Stapler Having a Powered Handle," dated May 11, 2023, 14 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.
European Patent Office, Extended European Search Report for European Application No. EP 23185918.2, entitled "Surgical Stapler Having Actuation Mechanism with Rotatable Shaft," dated Sep. 22, 2023, 5 pgs.
European Patent Office, Extended European Search Report for European Application No. EP 23198045.9, entitled "Reload Shaft Assembly for Surgical Stapler," dated Oct. 25, 2023, 12 pgs.

* cited by examiner

MATERIAL COMBINATIONS AND PROCESSING METHODS FOR A SURGICAL INSTRUMENT

CROSS-REFERENCE TO RELATED APPLICATIONS

This application is a continuation of U.S. patent application Ser. No. 17/514,180 entitled "Material Combinations and Processing Methods for a Surgical Instrument" filed on Oct. 29, 2021, currently pending, which claims priority to and benefit of U.S. Provisional Patent Application Ser. No. 63/107,321 entitled "Material Combinations and Processing Methods for a Surgical Instrument" filed on Oct. 29, 2020, each of which is incorporated herein by reference in its entirety.

BACKGROUND OF THE INVENTION

Field of the Invention

The present application relates generally to surgical instruments and, more particularly, to material combinations and processing methods for sliding components in end effectors of surgical instruments such as surgical stapling devices.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

Surgical staplers can further include replaceable reload cartridges such that multiple cartridges can be used with a stapler in a single surgical procedure. Surgical stapler clamping and firing mechanisms can include metallic components in sliding contact. Further improvements to components that are in sliding contact are desirable to resist wear degradation over multiple firing cycles.

SUMMARY OF THE INVENTION

In certain embodiments, a surgical stapling instrument is provided herein. The surgical stapling instrument comprises an end effector and a firing member. The end effector comprises a first jaw and a second jaw pivotably coupled to the first jaw. The firing member is longitudinally slidable with respect to the end effector to pivotably move the second jaw with respect to the first jaw and actuate the end effector. At least one of the first jaw, the second jaw, and the firing member comprises: a metallic substrate, a dry film surface coating disposed on the metallic substrate, and a bone wax layer disposed on the dry film surface.

In certain embodiments, a surgical stapler is provided herein. The surgical stapler comprises an elongate shaft and a jaw assembly. The elongate shaft extends from a proximal end to a distal end. The jaw assembly is positioned at the distal end of the elongate shaft. The jaw assembly comprises a cartridge support, an anvil, and a firing member. The cartridge support is configured to receive a reload cartridge having a plurality of staples disposed therein. The cartridge support and the anvil are pivotably movable between an open and a closed configuration. The firing member is longitudinally slidable in engagement with the cartridge support and the anvil in the closed configuration to fire staples. At least one of the anvil, the cartridge support, and the firing member comprises: a case hardened metallic substrate, a dry film surface coating disposed on the metallic substrate, and a bone wax layer disposed on the dry film surface.

In certain embodiments, a method of manufacturing a surgical end effector is provided herein. The method comprises providing a first jaw member, a second jaw member, and a firing member, each comprising a metallic substrate. The method further comprises hardening the metallic substrate of at least one of the first jaw member, the second jaw member, and the firing member to a first predetermined hardness. The method further comprises applying a dry film coating to the hardened at least one of the first jaw member, the second jaw member, and the firing member. The method further comprises applying a bone wax composition to at least one of the first jaw member, the second jaw member, and the firing member.

DETAILED DESCRIPTION OF THE INVENTION

Figure 1:
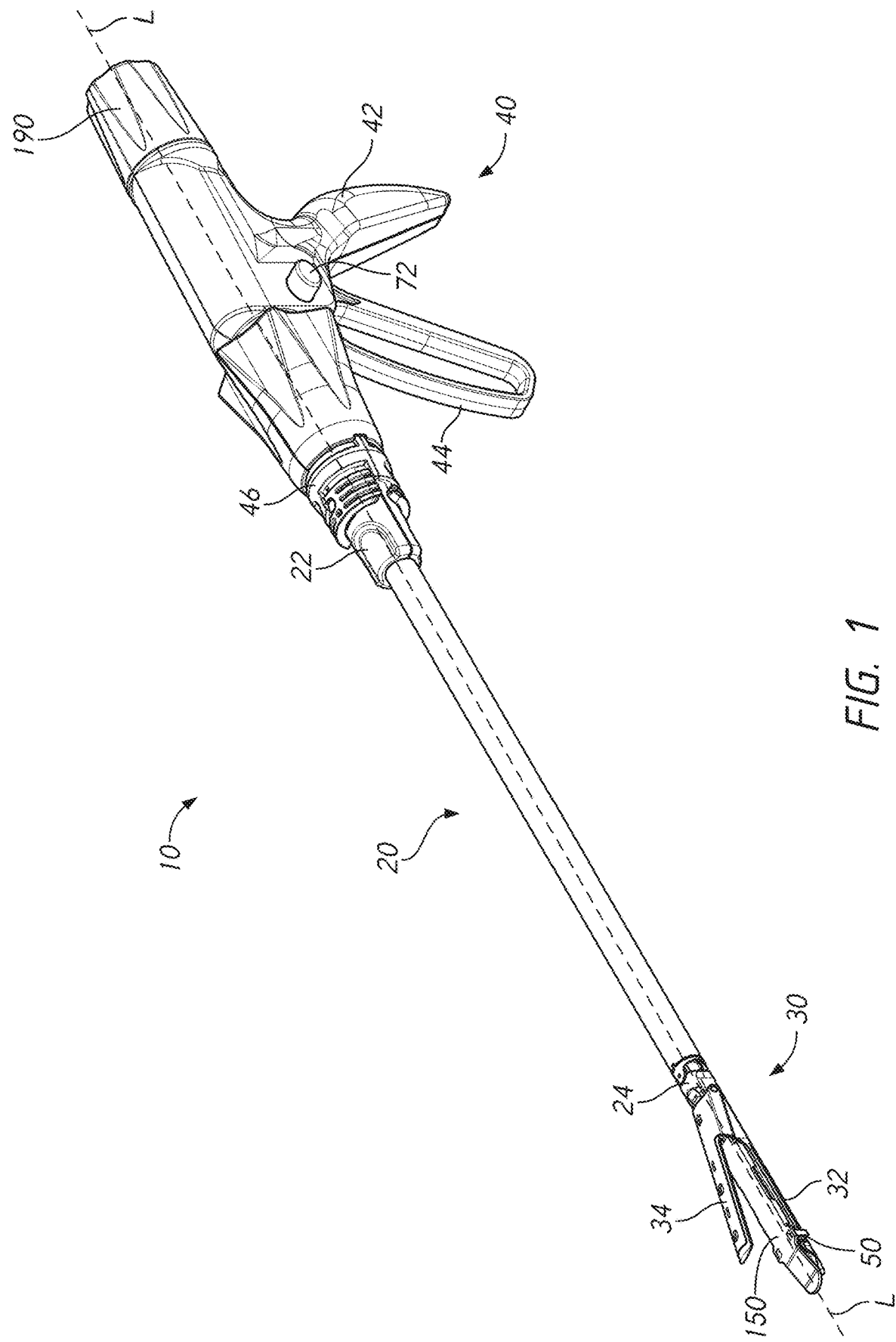
FIG. 1 is a perspective view of an embodiment of surgical stapling device.
Figure 2:
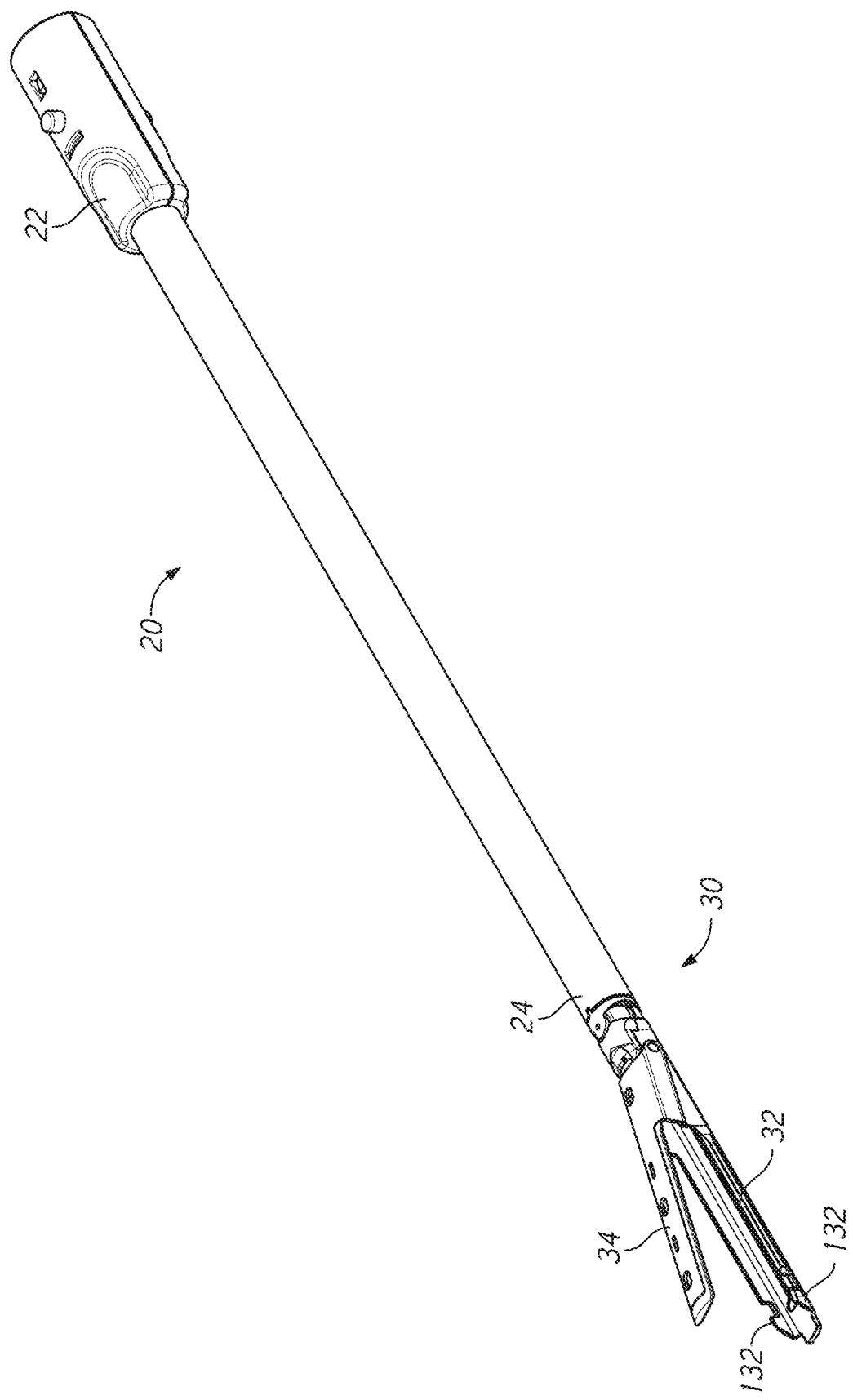
FIG. 2 is a perspective view of an embodiment of shaft assembly and jaw assembly for use with the surgical stapling device of FIG. 1.

With reference to FIGS. 1-2, embodiments of surgical stapling device are illustrated. The illustrated embodiment of surgical stapler 10 comprises an elongate shaft 20, a jaw assembly 30, and a handle assembly 40. Various aspects of the elongate shaft 20 and jaw assembly 30 described herein can be used interchangeably with either a mechanical handle assembly 40, as illustrated, or a powered handle assembly including, for example, an electric motor. Moreover, it is contemplated that aspects of the elongate shaft 20 and jaw assembly 30 described herein can be used in connection with a shaft assembly configured to be actuated by a robotic surgical system. FIG. 1 illustrates the surgical stapler 10 with the jaw assembly 30 in an open configuration. FIG. 2 illustrates a removable reload shaft assembly comprising the elongate shaft 20 and jaw assembly 30 of the surgical stapler 10 with the jaw assembly 30 in an open configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, an elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 34 pivotally coupled to a second jaw 32. In the embodiment illustrated in FIGS. 1-2, the jaw assembly is articulably coupled to the elongate shaft such that the jaw assembly can be selectively positioned at an articulated position with respect to the central longitudinal axis L. The handle assembly of FIG. 1 includes an articulation knob 190 and articulation mechanism configured to provide continuously selectable articulation of a jaw assembly of an elongate shaft assembly through an articulation range. In an initial configuration, the second jaw 32 includes a plurality of staples positioned within a reload cartridge 50 positioned therein. Thus, the second jaw 32 defines a reload support.

With continued reference to FIGS. 1 and 2, in the illustrated embodiment, the jaw assembly 30 can be actuated from an open configuration (FIG. 1) to a closed configuration to a stapling configuration by an actuation member or beam that is longitudinally slidable within the elongate shaft. In an initial position, the beam can be positioned at the distal end 24 of the elongate shaft 20. With the beam in the initial position, the first jaw 34 is pivoted away from the second jaw 32 such that the jaw assembly 30 is in the open configuration. The actuation beam engages the first jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the second jaw 32 such that further translation of the actuation beam distally past the first distance deploys the plurality of staples 36 from the second jaw 32.

Figure 3:
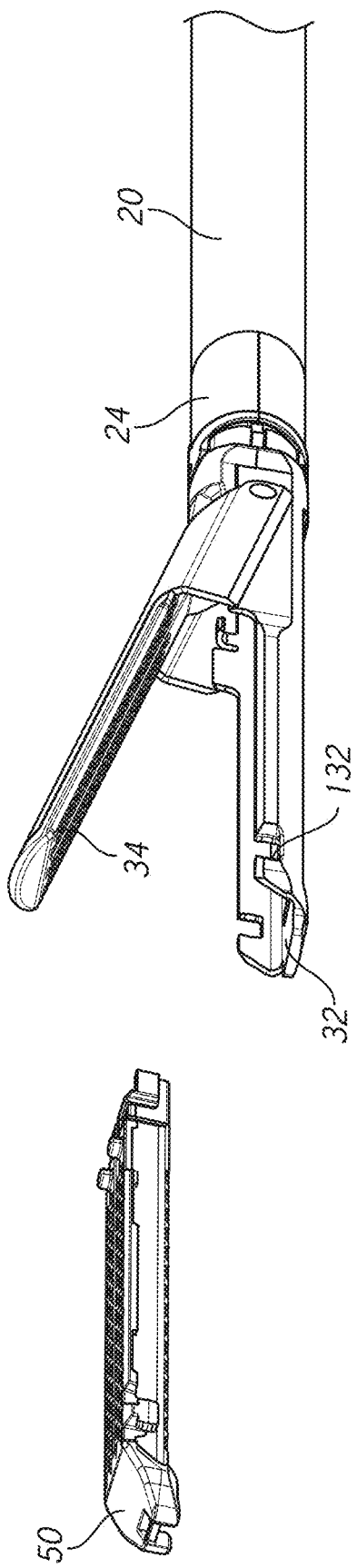
FIG. 3 is a perspective view of an embodiment of jaw assembly and reload cartridge for use with the surgical stapling device of FIG. 1.

With reference to FIGS. 1-3, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. The handle assembly 40 houses an actuation mechanism configured to selectively advance an actuation shaft responsive to movement of the movable handle 44 to actuate the actuation beam within the elongate a shaft a first distance in an open-close stroke to close the jaw assembly from an initial open position, a second distance beyond the first distance in a firing stroke to fire staples, and to return the actuation beam the second distance and the first distance to an initial position. In certain embodiments, a sliding selector 72 on the handle assembly can allow a user to select whether the handle assembly operates to actuate a jaw assembly in an open-close stroke or a firing stroke. Various embodiments of handle assemblies and associated actuation mechanisms are disclosed in U.S. Pat. No. 9,668,732, entitled "Surgical Stapler Handle Assembly Having Actuation Mechanism With Longitudinally Rotatable Shaft" and U.S. patent application Ser. No. 15/485,620, filed Apr. 12, 2017, entitled "Surgical Stapler Having Articulation Mechanism," both of which are incorporated by reference herein in their entireties.

With continued reference to FIGS. 1-3, in some embodiments, the surgical stapler 10 can include the plurality of staples positioned in a disposable reload cartridge 50 while the handle assembly 40 and elongate shaft 20 is configured to be reused with multiple staple reload cartridges. In certain embodiments, each reload cartridge 50 can be coupled to a reload cover 150 to shield a tissue contact surface and staple pockets of the reload cartridge before installation to the jaw assembly and that is to be removed before the surgical stapler is introduced to a surgical site. It can be desirable that the handle assembly 40 and elongate shaft 20 can resist wear-related performance degradation such that the stapler can reliably be actuated for multiple clamping and staple firing cycles, each comprising a single use reload cartridge 50. The surgical stapler can include the one or more grasping and firing lockout mechanisms that can limit functionality of the handle assembly to alert a user and enhance patient safety if no reload cartridge is present in the jaw assembly or if a partially or fully fired reload cartridge is present in the jaw assembly. In certain embodiments, a staple deployment member, such as a translatable sled or slider within the reload cartridge 50 can defeat one or more lockout mechanisms when the staple deployment member is in a proximal position in the jaw assembly, corresponding to an unfired reload cartridge is present in the surgical stapler 10.

With reference to FIG. 1, the handle assembly 40 includes a coupler 46 at the distal end thereof. The coupler 46 is adapted to engage the elongate shaft 20 of the surgical stapler 10. The coupler 46 can have a bayonet connection having an outer connector that can removably couple the handle assembly 40 to the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable shafts and/or reload cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

As noted above, the shaft assemblies, jaw assemblies, and reload cartridges described herein can also be used in conjunction with a powered stapler handle assembly or an actuator of a robotic surgical system. Various embodiments of powered handle assemblies and associated actuation mechanisms are disclosed in U.S. patent application Ser. No. 15/486,227, filed Apr. 12, 2017, entitled "Reload Shaft Assembly for Surgical Stapler;" U.S. patent application Ser. No. 15/486,008, filed Apr. 12, 2017, entitled "Surgical Stapler Having a Powered Handle;" and U.S. patent application Ser. No. 16/287,748, filed Feb. 27, 2019, entitled "Surgical Stapler Having a Powered Handle;" all of which are incorporated by reference herein in their entireties.

With reference to FIG. 3, a perspective view of the jaw assembly of the elongate shaft 20 is illustrated with the reload cartridge 50 removed from the second jaw 32. As illustrated, the reload cartridge 50 is removably positionable in the reload support defined by the second jaw 32. In the illustrated embodiment, the reload cartridge 50 includes a plurality of staples disposed therein, each staple positioned in its own staple pocket formed through a body of the reload cartridge. An upper surface of the reload cartridge 50 defines a tissue contact surface which, in certain embodiments, can be substantially planar. The reload cartridge further comprises a blade channel formed therein. As illustrated, the blade channel longitudinally extends between rows of staple pockets such that translation of a cutting blade through the blade channel transects tissue between rows of staples that have been deployed into tissue positioned in the jaws when staples are fired. The reload support defined by the second jaw 32 comprises a channel sized and configured to removably receive the reload cartridge 50. For example, in certain embodiments, the channel of the reload support can comprise at least one recess 132 sized and configured to receive a corresponding protruding boss on the reload cartridge 50.

Figure 4:
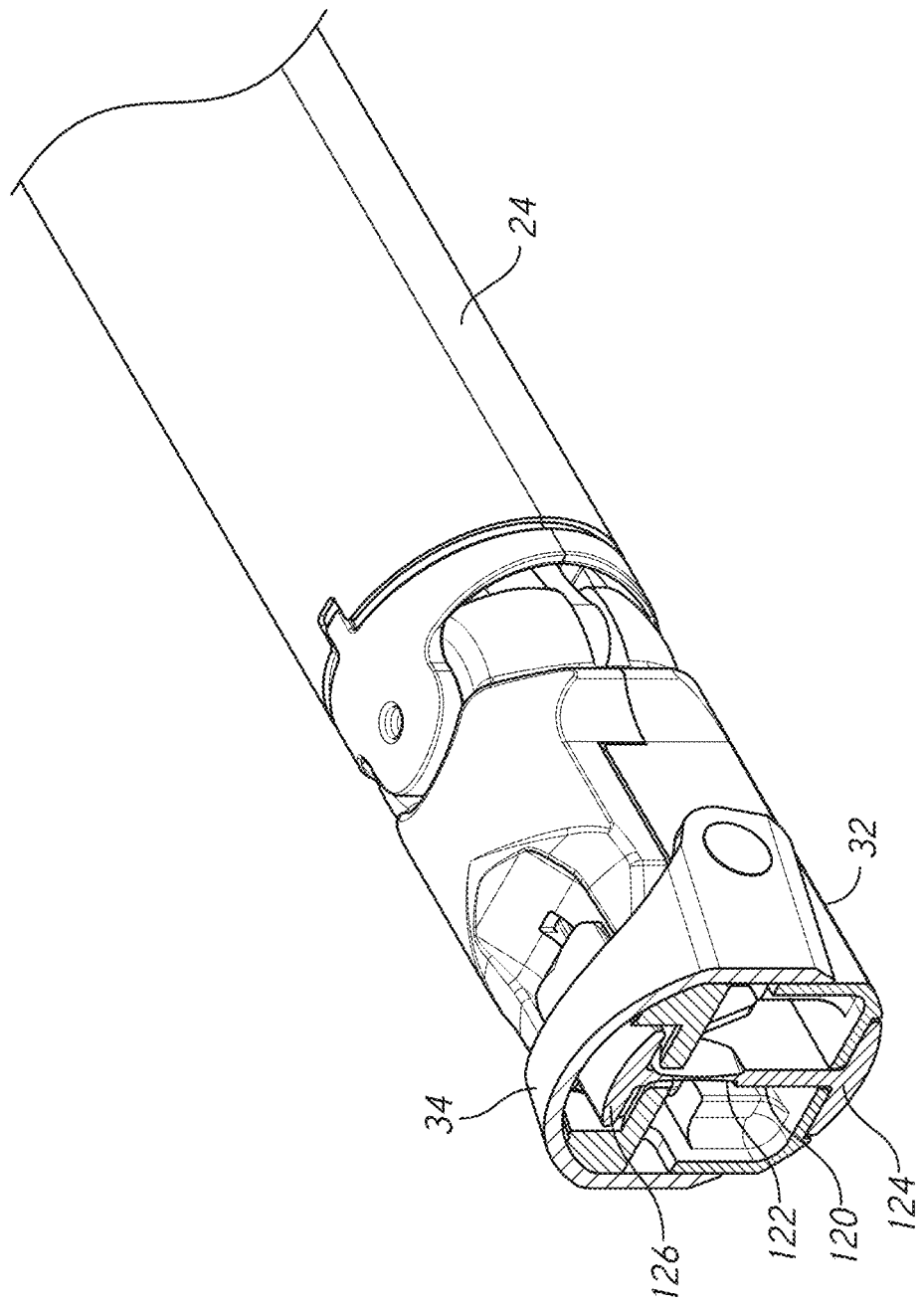
FIG. 4 is a cross sectional perspective view of a proximal end of the jaw assembly of FIG. 3.

With respect to FIG. 4, an embodiment of jaw assembly is illustrated. A cross section of the jaw assembly has been made generally perpendicularly to a longitudinal axis of the jaw assembly at a proximal end of the jaw assembly just distal the distal end 24 of the elongate shaft to facilitate visibility of certain aspects of operation of the surgical stapler in closure/tissue clamping and firing operations. In the illustrated embodiment, the surgical stapler comprises an actuation mechanism comprising a firing member 120 longitudinally translatable within the first jaw 34 and second jaw 32 of the jaw assembly to actuate the jaw assembly from an open configuration to a closed configuration and subsequently to fire a plurality of staples from a reload cartridge.

With continued reference to FIG. 4, in certain embodiments, the firing member 120 can comprise an I-beam profile with an upper flange 126 connected to a lower flange 124 by a vertical blade member 122. The upper flange 126 is translatable within a channel in the first jaw 34, and the lower flange 124 is translatable within a channel in the second jaw 32. The blade member 122 is translatable within the blade channel of the reload cartridge.

Figure 5:
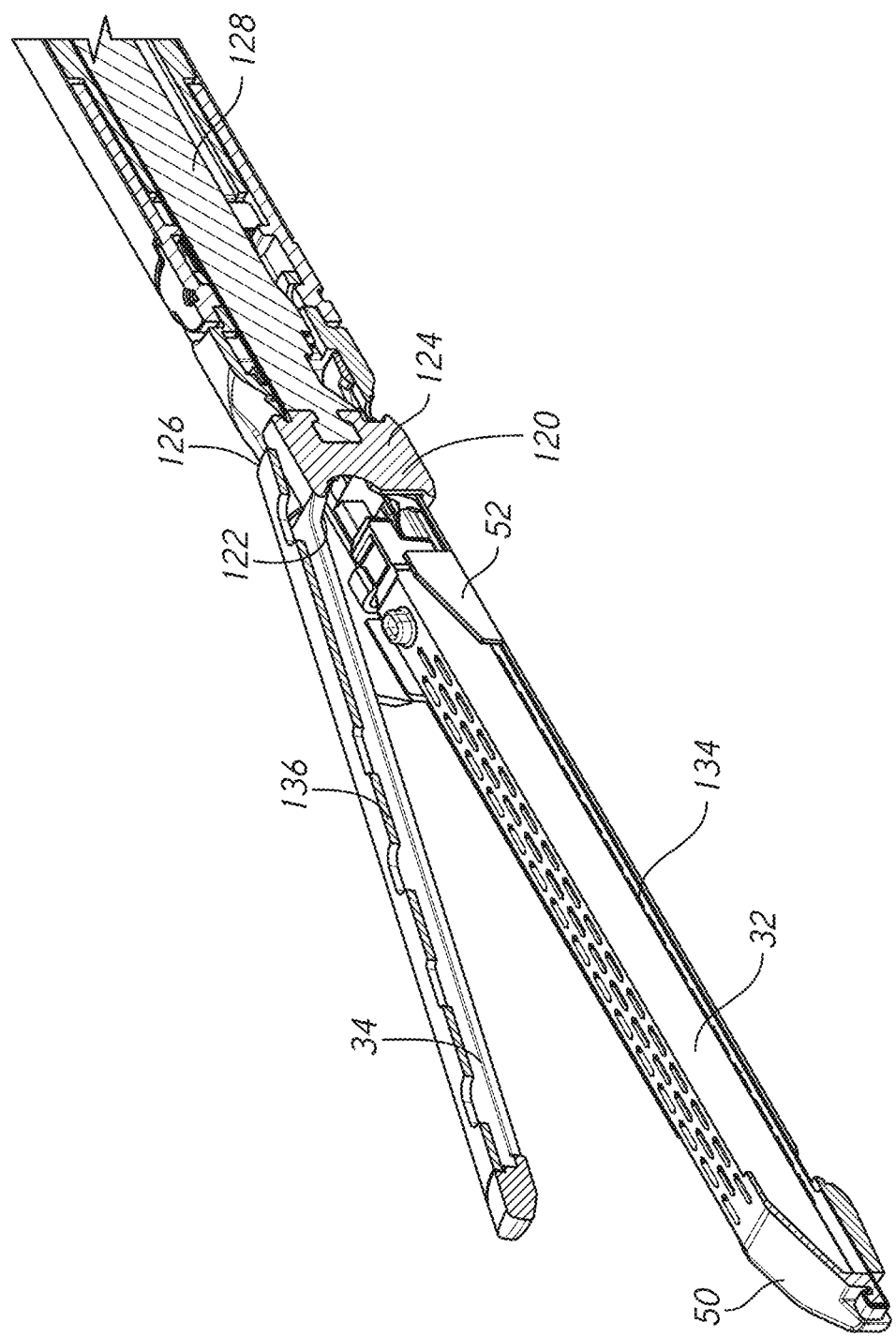
FIG. 5 is a cross sectional perspective view of the jaw assembly of FIG. 3.

With reference to FIG. 5, certain aspects of an embodiment of jaw assembly of a surgical stapler are illustrated. A cross section of the jaw assembly is illustrated taken longitudinally to further illustrate operation of the actuation mechanism of the surgical stapler. As illustrated, the elongate shaft comprises an actuation member 128 longitudinally slidable therein. The actuation member 128 extends to a distal end to which the firing member 120 is coupled. The reload cartridge 50 can comprise a slider 52 or wedge sled that translates therein, advanced by longitudinally distal movement of the firing member 120 to fire the plurality of staples from the reload cartridge.

With continued reference to FIG. 5, the jaw assembly can comprise an upper channel 136 formed in the first jaw 34. The jaw assembly can further comprise a lower channel 134 formed in the second jaw 32. In the illustrated embodiment, as the firing member 120 is advanced longitudinally to close the jaw assembly and fire staples from the reload cartridge 50, the upper flange 126 slides within the upper channel 136 of the first jaw 34, and the lower flange 124 slides in the lower channel 134 of the second jaw 32. In the illustrated embodiment, a proximal end of the upper channel 136 comprises a ramp such that actuation of the firing member 120 over the ramp pivots the first jaw 34 to a closed configuration. The upper channel 136 further comprises a channel distal the ramp extending such that it is generally parallel to the lower channel 134 with the jaws in the closed configuration.

As it is contemplated that the jaw assembly can be reused with multiple single use reload cartridges 50, it is desirable that sliding surfaces of the firing member 120 and lower and upper channels 134, 136 be configured to minimize performance degradation over multiple use cycles. With tissue clamped between jaws, a lower surface of the upper flange 126 slides against an upper surface of the upper channel 136, and an upper surface of the lower flange 124 slides against a lower surface of the lower channel 134. Accordingly, in certain embodiments, at least these sliding surfaces can be configured to reduce the impacts of frictional engagement therebetween. In other embodiments, it can be desirable that all of the first jaw 34, the second jaw 32, and the firing member 120 be configured to reduce impacts of frictional engagement therebetween.

In certain embodiments, it is desirable that the jaw assembly be configured to be reused with at least ten reload cartridges without significant performance degradation. In certain embodiments can be preferable that the jaw assembly be configured to be reused with at least twelve reload cartridges without significant performance degradation. Furthermore, it is contemplated that it is desirable that the jaw assembly is configured to be operable with a desired number of reload cartridges with an operating load of at least 80 pounds of compressive force applied by first and second jaws 34, 32 to tissue clamped therebetween. In other embodiments, it is desirable that the jaw assembly is configured to be operable with the desired number of reload cartridges with an operating load of at least 100 pounds of compressive force. In still other embodiments, it is desirable that the jaw assembly is configured to be operable with the desired number of reload cartridges with an operating load of at least 120 pounds of compressive force. In certain embodiments, the jaw assembly is configured to be operable with the desired number of reload cartridges at a desired operating load with the jaws misaligned at an angular deviation of up to one degree from the first jaw 34 parallel to the second jaw 32 in a closed configuration. In certain embodiments, the jaw assembly is configured to be operable with the desired number of reload cartridges at a desired operating load with the jaws misaligned at an angular deviation of up to two degrees from the first jaw 34 parallel to the second jaw 32 in a closed configuration. In use, misalignment between the jaws can occur during a stapling operation due to deflection of the jaws in response to the thickness or density of tissue clamped between the jaws.

In general, when two surfaces, such as the lower and upper flanges 124, 126 of the firing member and the respective lower and upper channels 134, 136, are in contact under load and they slide relative to one another, a frictional force opposes the motion. The frictional force is proportional to the load, but ultimately does not depend on the contact area. At the microscopic level, each of the surfaces is not truly flat, but rather has surface irregularities or asperities. These irregularities create localized contact points across which the contact load is distributed. The real contact area is then only a small fraction of the apparent, nominal area. There are multiple types of wear that can either lead to gradual increases in the coefficient of friction When asperities first touch, they deform elastically. However, even small loads when concentrated over a small area can cause large contact stresses that are high enough to cause plastic deformation. The contact points then flatten, forming junctions. Wear in general involves the physical removal of material from a solid object. It can be divided into three categories: abrasive, adhesive and fatigue. Abrasive wear is a more gradual wear process. It occurs when two surfaces rub against one another and the harder surface grinds the softer away. It is often characterized by a rough appearance and can involve the creation of particulate. In many cases, some work hardening (cold working) can occur during this stage. Adhesive wear is a more aggressive form of wear that can lead to galling, especially with metal-to-metal contacting wear surfaces. Highly localized temperatures and the peaks of opposing asperities can deform and move together. Failure to clear debris further exacerbates this type of wear leading to galling with high friction forces.

Figure 6:
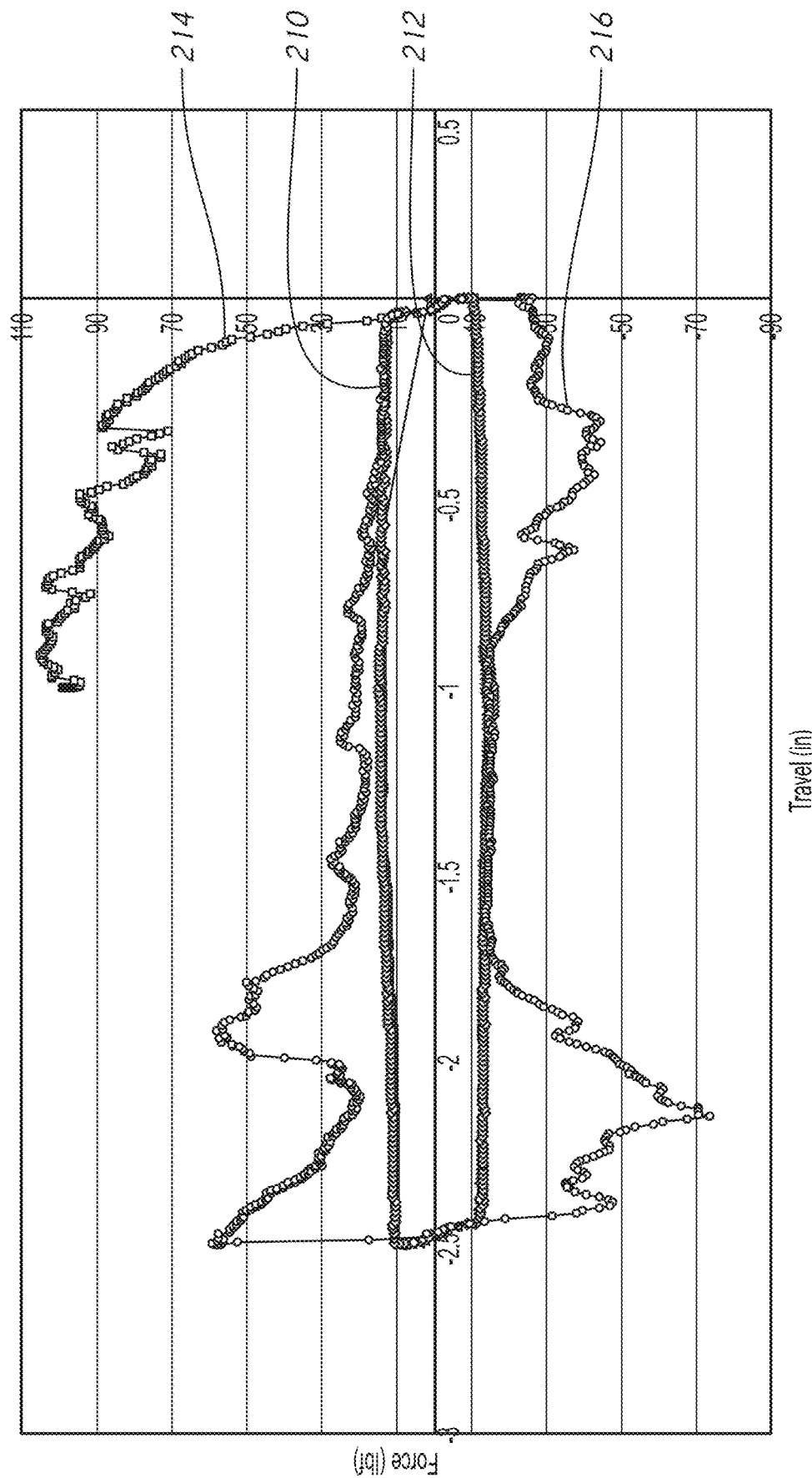
FIG. 6 is a graph showing an illustrative force versus travel plot for an exemplary embodiment of jaw assembly.
Figure 7:
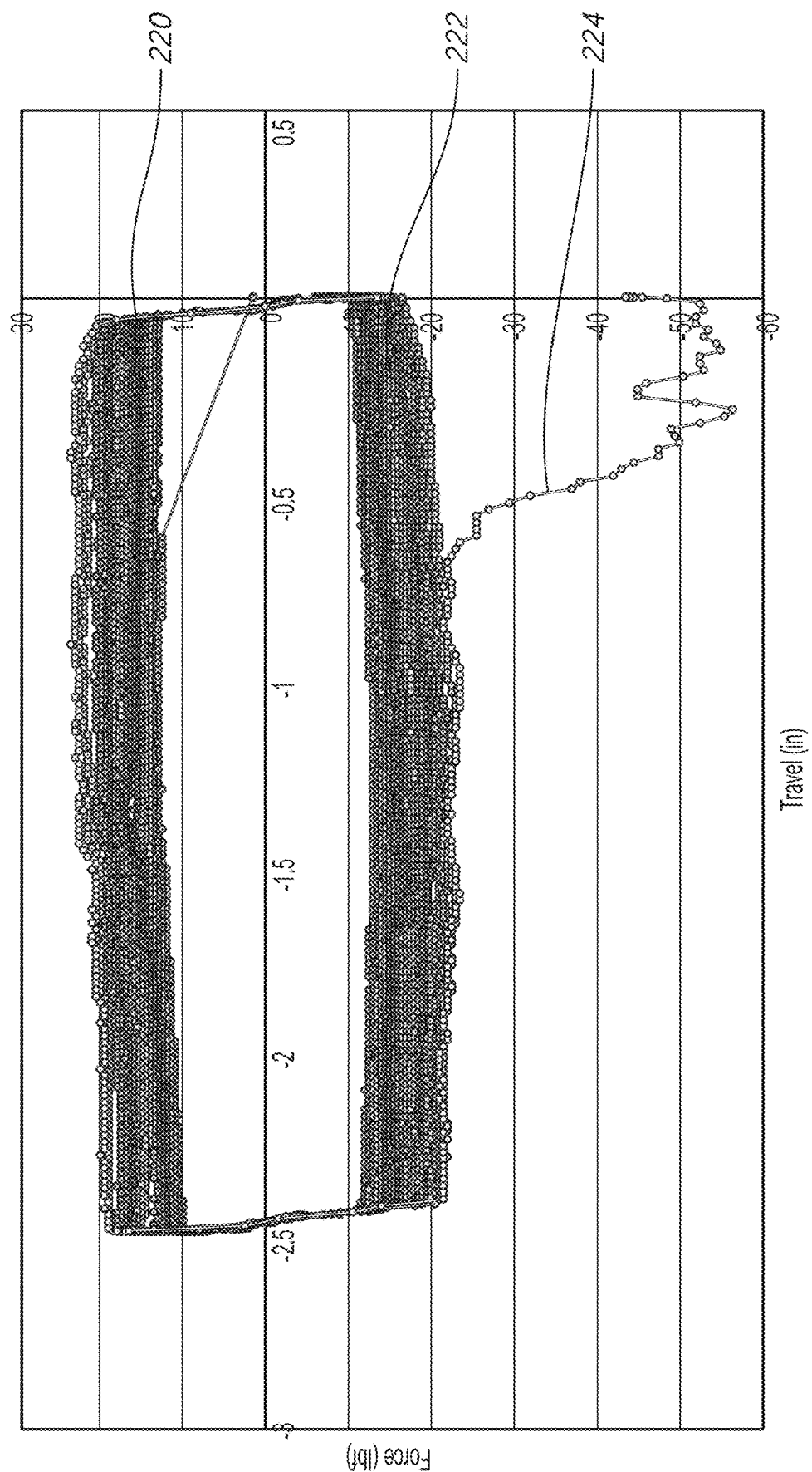
FIG. 7 is a graph showing an illustrative force versus travel plot for another exemplary embodiment of jaw assembly.
Figure 8:
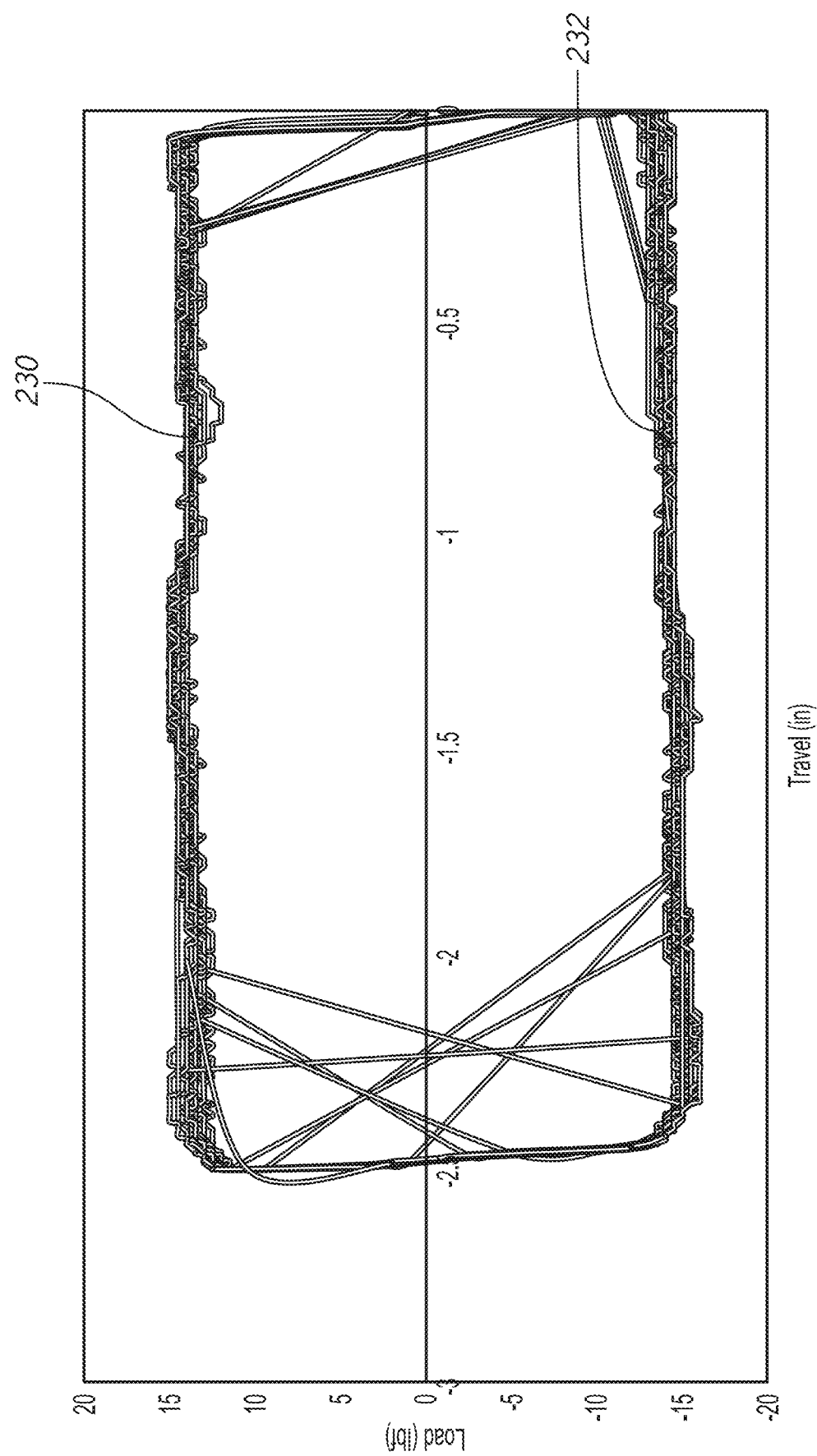
FIG. 8 is a graph showing an illustrative force versus travel plot for another exemplary embodiment of jaw assembly.

With reference to FIGS. 6-8, certain aspects of sliding engagement between two surfaces are illustrated. Force versus distance plots for exemplary combinations of sliding engagement cycles between a pair of exemplary components are illustrated. FIG. 6 illustrates a force versus distance plot for exemplary components over several sliding engagement cycles illustrating abrasive wear and galling. FIG. 7 illustrates a force versus distance plot for exemplary components over several sliding engagement cycles illustrating a plurality of cycles of abrasive wear followed by galling. FIG. 8 illustrates a force versus distance plot for exemplary components over several sliding engagement cycles illustrating gradual abrasive wear.

With reference to FIG. 6, an illustrative force versus distance plot for several sliding engagement cycles between exemplary sliding components is illustrated. The plot illustrates a progression from at least one sliding engagement cycle with abrasive wear in a first direction 210 and abrasive wear in a second direction 212 to galling wear in a first direction 214 and galling wear in a second direction 216. When the components are moved in the first and second directions with abrasive wear, a friction force between the components is relatively low and relatively constant along a distance traveled. A plot line above the x-axis indicates travel in a first direction (210, 214) while a plot line below the x-axis indicates travel in a second direction (212, 216) opposite the first direction. The height (or depth) of a plot line from the x-axis represents the frictional force required to slide the components. When galling wear is encountered in the first and second directions 214, 216, the frictional force is highly irregular and significantly larger than the frictional force encountered in the abrasive wear regime. Galling is highly detrimental to the function of the device as it increases the coefficient of kinetic friction by a factor greater than one, which as a result multiplies the force required to actuate the device considerably. In some instances, galling can cause the input force required to actuate the device to increase to more than double what it is expected to be for a pair of sliding surfaces. Thus, an embodiment of surgical stapler with sliding components experiencing galling wear after several sliding engagements would be undesirable for use with multiple reload cartridges as the force required to actuate the actuation mechanism would be excessive, stressing components in the shaft assembly and handle assembly, and making the handle assembly difficult to operate.

With reference to FIG. 7 an illustrative force versus distance plot for several sliding engagement cycles between exemplary sliding components is illustrated. The plot illustrates a progression from at least several sliding engagement cycles with abrasive wear in a first direction 220 and abrasive wear in a second direction 222 to galling wear in a second direction 224. When the components are moved in the first and second directions with abrasive wear, a friction force between the components is relatively low and relatively constant along a distance traveled, although the plot line illustrates a plurality of wear cycles with progressively increasing friction forces until galling occurs. In certain embodiments, components exhibiting such wear characteristics can be used in a surgical stapler provided that the components remain in the abrasive wear regime over a sufficient number of wear cycles to permit use of at least a desired number of reload cartridges before experiencing galling wear.

With reference to FIG. 8 an illustrative force versus distance plot for several sliding engagement cycles between exemplary sliding components is illustrated. The plot illustrates repeated operation over a plurality of sliding engagement cycles with abrasive wear in a first direction 230 and abrasive wear in a second direction 232 without the components experiencing galling wear. When the components are moved in the first and second directions with abrasive wear, a friction force between the components is relatively low and relatively constant along a distance traveled with minimal increase from cycle to cycle. It is desirable to configure the jaw assembly for a surgical stapler to have wear characteristics that reduce the likelihood of galling for repeated use with multiple reload cartridges.

In certain embodiments, materials selection for components of a surgical stapler that engage in sliding contact, such as jaw assemblies and firing member can be selected based on certain priorities. For example, as an initial consideration, the materials selected, as well as surface preparation coatings and treatments thereof, are limited to those that meet standards for biocompatibility for use in a patient-contact surgical device. Moreover, it is desirable that the materials selected are able to be joined in a welding operation, which allows flexibility in construction of various aspects of a jaw design, such as by facilitating the use of a two-piece first jaw 34 having a cover or cap that is welded over lower, anvil surface first jaw member forming a channel therebetween. Further, it is desirable that the materials selected have sufficient strength and toughness characteristics for repeated staple firing operations. Additionally, it can be desirable that the materials selected resist oxidation and corrosion. Finally, it is desirable that the materials selected are manufacturable by a variety of processes to promote manufacturing efficiencies, including, for example metal injection molding processes.

Various grades of stainless steel can be selected to achieve the desired characteristics. For example, in certain embodiments, a grade 17-4 stainless steel can be selected for use in sliding components. In other embodiments, a grade 420 stainless steel can be selected for use in sliding components. Grade 420 is a martensitic stainless steel as opposed to a precipitation-hardened stainless steel such as grade 17-4. A grade 420 stainless steel has a relatively high carbon content as compared to a grade 17-4 stainless steel. Thus, desirably, a grade 420 stainless steel is relatively hardenable as compared to a lower-carbon steel. However, martensitic stainless steels tend to be less weldable than precipitation-hardened stainless as brittle martensite can tend to form from rapid cooling of weld zones that can lead to stress induced cracking. Moreover, the relatively higher carbon content of a grade 420 stainless steel can also lead to a relatively lower corrosion resistance. Each of grades 17-4 and 420 is suitable for use in a metal injection molding process.

With regard to material selection, in still other embodiments, a grade 13-8 or a grade 455/465 stainless steel can be selected for use. However, it is noted that these grades of stainless steels tend to be specialty materials, thus these grades of stainless steel may be less desired in view of potential cost, availability, and manufacturability concerns.

As material selection considerations indicate the desirability of metallic, stainless steel materials for use in the jaw assembly and firing member of a surgical stapler, further consideration should be made of preparation and processing the characteristics of these components to reduce the likelihood of galling, which can result from metal-to-metal sliding engagement. In general, materials having a relatively high surface hardness can be more resistant to galling wear. There are various techniques for achieving a relatively high surface hardness in a metallic substrate such as the stainless steel substrates considered for use in sliding components of a surgical stapler. For example, in various embodiments, at least one of: diffusion/thermal-chemical techniques, surface plating techniques, surface coating techniques, and applied energy techniques can be used to prepare a surface of a metallic substrate for use in sliding contact with reduced galling.

In diffusion or thermo-chemical processes a surface layer of a metallic substrate is hardened through the addition of a hardening species such as carbon, nitrogen, or boron at, typically, a relatively high temperature. These processes can be termed 'case hardening' in that a goal is to create a relatively hard case or surface layer while maintaining the toughness and ductility of the core. However, typical case hardening techniques have had undesirable consequences on stainless steel materials, especially precipitation hardened stainless steel materials in that typical case hardening techniques have decreased corrosion resistance of a stainless steel material. Moreover, with precipitation hardened stainless steel materials, case hardening methods with relatively high temperatures can result in unintended annealing of the material. Additionally, where a metallic substrate has been formed using a metal injection molding process, the substrate can have relatively high porosity. Thus, the depth of a case hardened layer, absent further modification to the case hardening technique to control a hardened layer depth, may be different from that of a similarly hardened material metallic substrate not formed by a metal injection molding process.

However, certain case hardening techniques can be used on stainless steel materials with fewer or no significant undesirable effects. For example, a relatively low temperature diffusion case hardening technique commercially known under the trademarks S3P (Specialty Stainless Steel Processes) and KOLSTERISING offered by Bodycote plc. This diffusion technique can case harden relatively low carbon stainless steels such as grade 17-4 stainless steels with minimal reductions in corrosion resistance and minimal impact to the underlying strength and ductility of the metallic substrate.

Another technique to creating a hardened layer is through surface modifications to modify the grain structure of the metallic substrate at an outer layer through work hardening. For example, shot peening (impacting the substrate with high velocity shot) or ion implementation (impacting the metallic substrate with high velocity particles) processes can be used to form a hardened surface layer. Advantageously, these processes do not affect surface chemistry and thus should not reduce corrosion resistance. However, if foreign contaminants are present in the shot (for example if shot media is reused), the contaminants can become embedded in the metallic substrate and potentially cause localized sites of reduced corrosion resistance. Moreover, these surface modification processes can present manufacturing challenges as only the surfaces impacted are work hardened, requiring tight control of fixtures, shot size, intensity, and coverage to facilitate consistent results and reduce potential distortion of the substrate.

In certain embodiments, surface plating, that is, introducing a thin layer of metallic compounds on a substrate, can be used to create desired surface hardness properties for sliding components of a surgical stapler. Examples of types of material that can be used in surface plating to provide surface hardness include chrome, electroless nickel, Diamond Like Coating, and ceramics. Advantageously, depending on the material chosen, surface plating can be an immersive process that can be implemented at a component level with consistent surface properties. However, surface plating can affect the weldability of a component as the plating compound will become present in a welded matrix, impacting the strength of the component. Moreover, surface platings, with high hardnesses can also be relatively brittle and can undesirably tend to crack and particulate when heavily loaded in a point contact. In surgical stapler components, in certain instances the engagement of the flanges of the firing member can engage their respective channels at a substantially point contact, especially with misalignment of the jaws or when a large tissue section is clamped between the jaws.

In certain embodiments, a metallic substrate of a sliding component of a surgical stapler can have an applied surface coating to provide desired operation characteristics. However, in general, surface coatings do not adhere as well to a metallic substrate as surface platings. Moreover, similar to surface plating, surface coatings may particulate when loaded in use. Accordingly, it is preferable to use biocompatible surface coating materials. Additionally, surface coatings, if applied before welding a material substrate, may form part of the weld matrix and reduce strength of a welded component. Accordingly, masking a weld site or coating after a welding operation can be selected to minimize the impact of surface coatings on substrate weldability.

Various surface coatings can be applied to a metallic substrate to improve sliding performance. For example, in certain embodiments, lubricants such as those commercially available under the trademark KRYTOX from the Chemours Company, or MOLYKOTE from the Dow Corning Corporation can be applied to sliding surfaces. In other embodiments, a dry film polytetrafluoroethylene (PTFE) coating can be applied to sliding surfaces to increase lubricity therebetween. For example, a coating commercially available as Dry Film RA coating from the Donwell Company, Inc. can be applied to sliding components of a surgical instrument. PTFE dry film materials can be suitable for use in patient contact applications and can be applied strategically by a spraying process or at a component level through an immersive process.

In certain embodiments, bone wax can be applied as a surface coating to improve sliding performance by acting as a lubricant between sliding surfaces. Various bone wax compositions are commercially available and typically comprise primarily beeswax. Bone wax is suitable for use in patient contact applications as it has been traditionally applied to reduce bleeding from bone surfaces during a medical procedure. Desirably, bone wax is tacky and holds well to applied surfaces. Moreover, bone wax typically only undergoes minimal particulation even with point contact engagement between sliding surfaces. However, bone wax can have a relatively low melting transition temperature (it can be approximately 120 F for certain bone wax compositions). Accordingly, consideration of anticipated sterilization and shipping temperature ranges must be assessed to reduce the likelihood of melting and pooling of applied bone wax. Moreover, bone wax is typically manually applied to target surfaces, thus consistent application to recessed surfaces such as jaw assembly channels can require specialized application tools and procedures.

Figure 9A:
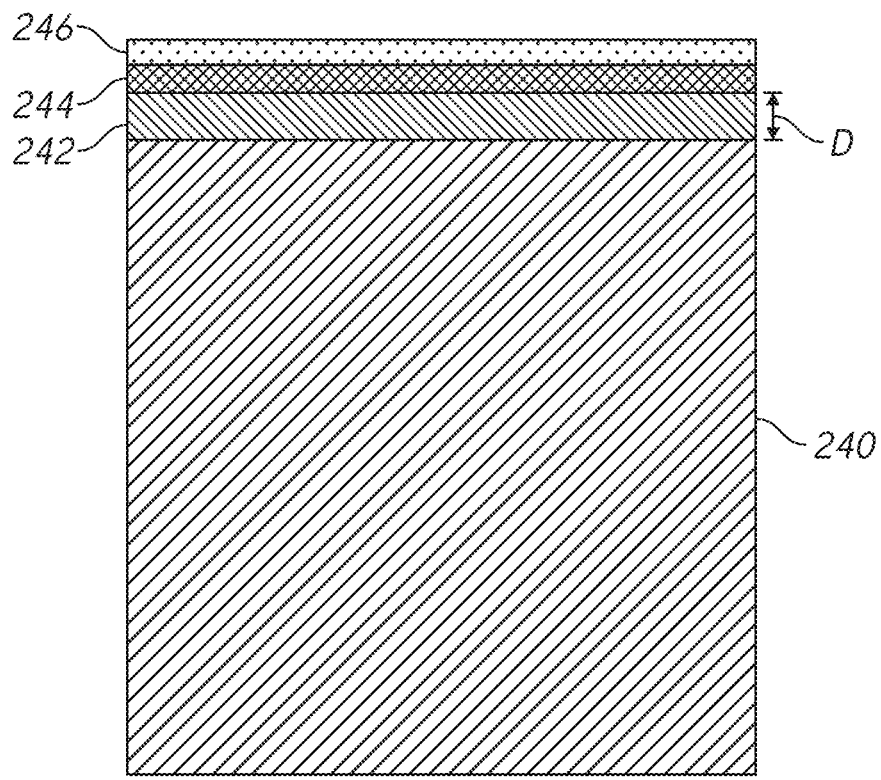
FIG. 9A is a schematic illustration of a cross section of a metallic substrate for an exemplary embodiment of a component of a surgical stapler.

With reference to FIG. 9A, a schematic cross section for a surface of a metallic substrate for use as a sliding surface of a surgical stapling device is illustrated. As discussed above, in view of various considerations for material selection, stainless steel materials are desirable for use in sliding components of a surgical stapling device, such as a firing member and jaw members of a jaw assembly of a surgical stapler. However, in metal-to-metal sliding engagements, these materials can undesirably be subject to galling wear. Accordingly, it is desirable to prepare the sliding surfaces to resist galling. In the illustrated embodiment, the component comprises a metallic substrate 240 having a first strength and a first hardness. A surface layer 242 of the metallic substrate 240 is hardened to a second hardness greater than the first hardness. For example, in certain embodiments, a case hardening method is used to create the surface layer 242 having a depth D at the second hardness. In some embodiments, a diffusion method is used in the case hardening method. In certain embodiments, a low-temperature diffusion case hardening method is used.

With continued reference to FIG. 9A, in certain embodiments, a first surface coating layer 244 can overlie the metallic substrate 240 and a hardened surface layer 242 thereof. For example, in some embodiments, it can be desirable that a first surface coating be selected to limit metal-to-metal contact. Moreover, as certain case hardening methods can tend to reduce corrosion resistance in stainless steel materials, in certain embodiments, it can be desirable that a first surface coating layer can define an oxidation inhibition material.

With continued reference to FIG. 9A, in certain embodiments components of surgical stapler can further comprise a second surface coating layer 246 overlying the first surface coating layer 244. The second surface coating layer 246 can be selected to reduce wear over multiple sliding engagement cycles. For example, in certain embodiments, a bone wax composition can be disposed across sliding surfaces to provide sliding lubrication for multiple reload cycles. Advantageously, a bone wax composition can enhance sliding of components of a surgical stapler in sliding contact even with increases in point contact with inadvertent misalignment.

With continued reference to FIG. 9A, another aspect of surface preparation for sliding components of a surgical stapler is surface finish. For sliding surfaces, it can be undesirable that the surface finish of the sliding components be either relatively smooth, (for example, with a roughness<25 μin) or have a relatively high roughness (for example, with a roughness>75 μin). Sliding surfaces that are highly smooth have a relatively large theoretical contact area, with fewer surface asperities. Thus, these smooth surfaces can tend to facilitate galling and cold welding when in sliding engagement. In contrast, relatively high roughness surfaces can result in relatively high frictional forces and particulation as asperities bind relative to one another. Sliding surfaces having a relatively moderate roughness (for example between about 25 μin and 75 μin) can desirably have a reduced incidence of galling and moderate frictional forces as compared with relatively low roughness surfaces and relatively high roughness surfaces. A moderate roughness can also desirably retain a surface coating when the coated surface is in sliding engagement. In certain embodiments, a moderately rough surface, having a surface roughness between about 25 μin and 75 μin can be prepared through a tumbling process.

Figure 9B:
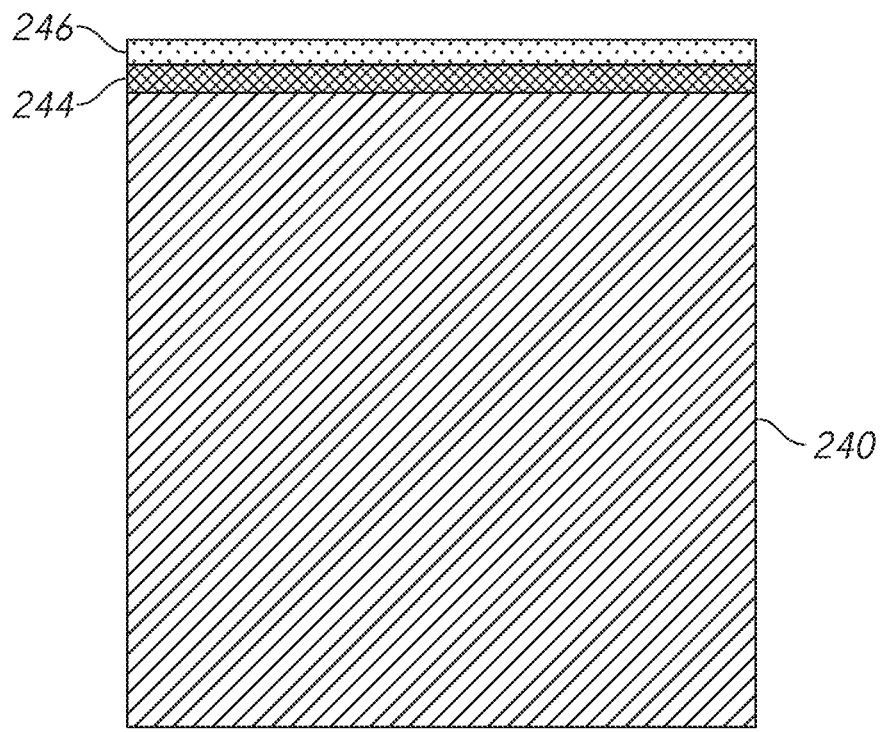
FIG. 9B is a schematic illustration of a cross section of a metallic substrate for another exemplary embodiment of a component of a surgical stapler.

With reference to FIG. 9B, a schematic cross section for a surface of another embodiment of metallic substrate for use as a sliding surface of a surgical stapling device is illustrated. Similar to the embodiment of metallic substrate illustrated above with reference to FIG. 9A, the illustrated embodiment of metallic substrate comprises a metallic substrate 240 core, a first coating layer 244, and a second coating layer 246. In certain embodiments, the first coating layer 244 can comprise a dry film, and the second coating layer can comprise a bone wax layer. However, unlike the embodiment of metallic substrate of FIG. 9A, as illustrated in FIG. 9B, the metallic substrate 240 does not comprise a case hardened surface.

In view of the above discussion, various embodiments of material selection and surface preparation to achieve desired sliding performance in a firing member, first jaw, and second jaw without galling over a desired number of firing cycles. In one embodiment, the firing member and jaws of the jaw assembly can comprise a grade 17-4 stainless steel material. The 17-4 stainless steel material can be heat treated to a H900 condition (corresponding to approximately 45 Rockwell C hardness). A surface layer of the material can be case-hardened to approximately 70 Rockwell C hardness. For example, in some embodiments a diffusion method such as an S3P method commercially available from Bodycote plc., can provide a hardened surface layer of approximately between 65 and 70 Rockwell C hardness at a case depth of approximately 25-40 microns. The firing member and jaws of the jaw assembly can be tumbled to a moderate surface roughness. For example, the components can have a surface roughness of between approximately 25 μin and 75 μin. In one embodiment, the components have a surface roughness of approximately 50 μin. A first coating layer of a PTFE dry film can be applied. This first coating layer can inhibit corrosion at the hardened surface and limit metal-to-metal contact. The components can further comprise a second coating layer of a bone wax composition. Advantageously, this combination of materials and processes results in a jaw assembly and firing member that resists galling when repeatedly used with a plurality of single use reload cartridges.

Another embodiment of firing member, first jaw, and second jaw of a surgical stapler comprises a grade 420 stainless steel material that has been heat treated to approximately 55 Rockwell C hardness. The components can be tumbled to a moderate surface roughness. The components can comprise a first coating layer of a PTFE dry film and a second coating layer of a bone wax composition.

Another embodiment of surgical stapler components including at least one of a firing member, a first jaw, and a second jaw comprises a grade 17-4 stainless steel material. The material is heat treated to approximately 45 Rockwell C hardness. For example, as described above, in certain embodiments, the material can be heat treated to an H900 condition. No further case hardening is provided. The components can have a moderately rough surface finish that can be achieved with a tumbling process. The components can comprise a first coating layer of a PTFE dry film and a second coating layer of a bone wax composition. In certain embodiments, one or more of the firing member, first jaw, and second jaw components can be formed of a grade 17-4 stainless steel material with a metal injection molding process. Certain metal injection molding processes can result in a metallic substrate with relatively high porosity relative to a counterpart machined component. Case hardening techniques on such a porous metal injection molded component can create a hardened surface layer having a relatively high depth, but correspondingly relatively high brittleness, which can impact the bulk properties of the case hardened component. Accordingly, embodiments of surgical stapler components without further case hardening processes can be desirable where the components are formed with metal injection molding processes that can create relatively porous metallic substrate.

While in the above embodiments, the components are prepared such that the surface hardnesses of the jaws and the firing members are relatively high (at least about 45 Rockwell C hardness up to about 70 Rockwell C hardness) and substantially identical. It is contemplated that in other embodiments, the firing member can have a slightly lower surface hardness than the jaw members. For example, the firing member can have a surface hardness up to approximately 10 Rockwell C hardness below that of the jaws.

Moreover, while in the above embodiments, case hardening is provided by diffusion or heat treatment, in other embodiments, it is contemplated that shot peening or another work hardening technique can be applied to work harden a surface layer of the metallic substrate of the components. This work hardened surface layer can then be coated with one or more coating layers With reference to FIG. 10 a method of preparing a metallic substrate for use as a sliding component of a surgical stapler is illustrated. In certain embodiments, the method can comprise providing a metallic substrate 260. As discussed above, in certain embodiments, the metallic substrate can comprise a stainless steel material such as a grade 17-4 stainless steel or a grade 420 stainless steel. In certain embodiments, providing the metallic substrate can comprise metal injection molding a metallic substrate component.

Figure 10:
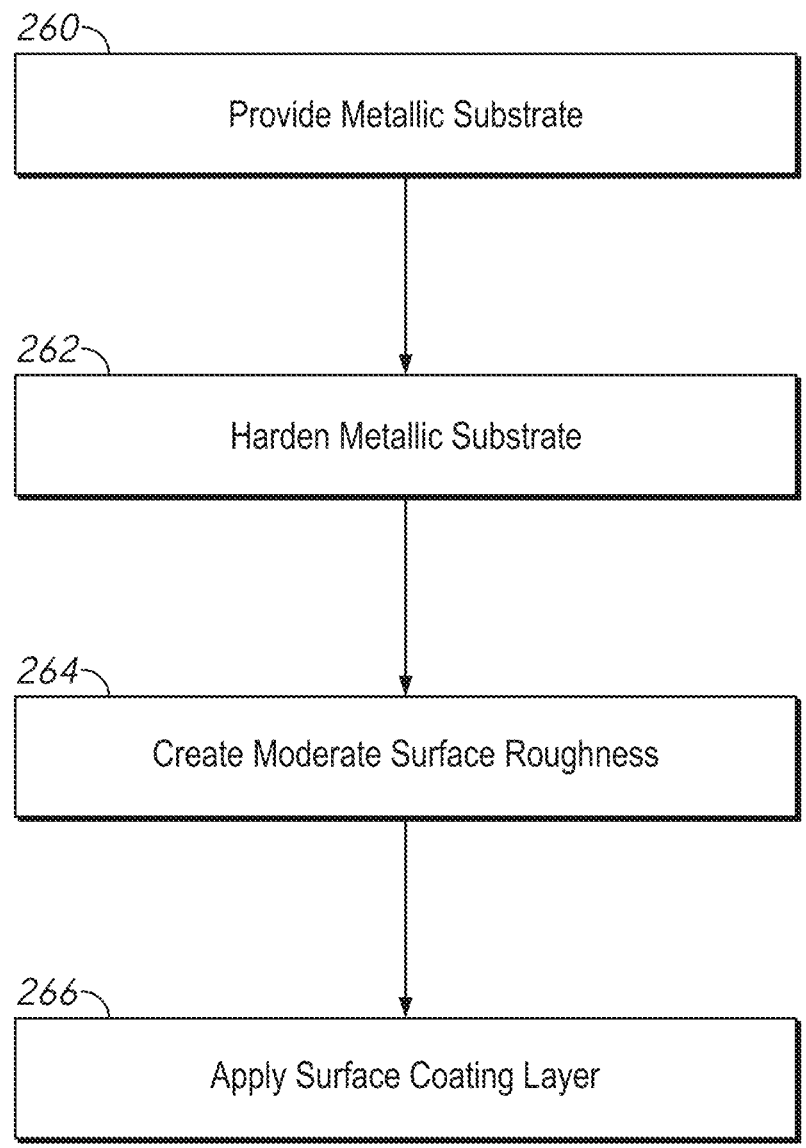
FIG. 10 illustrates an exemplary method for preparing a surface of a component of a surgical stapler.

With continued reference to FIG. 10, the method further comprises hardening the metallic substrate 262 to a desired hardness. In certain embodiments, hardening the metallic substrate can comprise heat treating the metallic substrate. For example, in certain embodiments, hardening the metallic substrate comprises heat treating the metallic substrate to a H900 condition corresponding to a hardness of approximately 45 HRC. In various embodiments, hardening the metallic substrate can comprise case hardening the metallic substrate with a diffusion process. In other embodiments, hardening the metallic substrate can comprise work hardening the surface layer of the metallic substrate such as by shot peening. In certain embodiments, such as schematically illustrated in FIG. 9B, the metallic substrate is hardened to a hardness of approximately 45 HRC by heat treatment without further case hardening. In other embodiments, such as schematically illustrated in FIG. 9A, the metallic substrate is hardened with a heat treatment process and subsequently case hardened such as with a diffusion process to achieve a relatively high surface hardness. In some embodiments, the surface layer can be hardened to between about 45 HRC and 75 HRC. It can be desirable that the surface layer is hardened to at least about 55 HRC. In certain embodiments, the surface layer is hardened to about 70 HRC. In certain embodiments, a metallic substrate to form firing member components for a surgical stapler is surface hardened to a first hardness, and a metallic substrate to form a first jaw and a second jaw is surface hardened to a second hardness different from the first hardness. In certain embodiments, the second hardness is within approximately 10 HRC greater than the first hardness.

With continued reference to FIG. 10, in certain embodiments, the method further comprises providing a moderate roughness surface finish 264. In certain embodiments providing a moderate roughness surface finish can comprise tumbling the components. In certain embodiments, the moderate roughness surface finish can comprise a surface roughness between approximately 25 µin and 75 µin. In some embodiments, the surface roughness is approximately 50 µin.

With continued reference to FIG. 10, in certain embodiments, the method further comprises applying at least one surface coating 266. In certain embodiments, applying at least one surface coating comprises applying a first surface coating and applying a second surface coating. In certain embodiments, applying at least one surface coating comprises applying a PTFE dry film and applying a bone wax composition.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A surgical instrument comprising:
   an end effector comprising:
     a first jaw comprising a first channel formed therein, and
     a second jaw pivotably coupled to the first jaw, the second jaw comprising
   a second channel formed therein; and
   a firing member longitudinally slidably engaged with the end effector to pivotably move the second jaw with respect to the first jaw and actuate the end effector, the firing member having an I-beam profile defined by an upper flange connected to a lower flange by a vertical blade member, the upper flange being slidable within the first channel and the lower flange being slidable within the second channel;
   wherein at least a portion of each of the first jaw, the second jaw, and the firing member that are in sliding engagement comprises a sliding surface configured to resist galling, the sliding surfaces each comprising a metallic substrate layer, a metallic surface layer, a first surface coating layer overlying the metallic surface layer, and a second surface coating layer overlying the first surface coating layer.

2. The surgical instrument of claim 1, wherein the metallic substrate layer has a first hardness and the metallic surface layer has a second hardness greater than the first hardness.

3. The surgical instrument of claim 2, wherein the hardness of the metallic surface layer is within the range of approximately 45 HRC to approximately 70 HRC.

4. The surgical instrument of claim 2, wherein the metallic surface layer comprises a case hardened surface.

5. The surgical instrument of claim 1, wherein the first surface coating layer comprises an oxidation inhibition material.

6. The surgical instrument of claim 1, wherein the first surface coating layer comprises a dry film PTFE coating.

7. The surgical instrument of claim 1, wherein the second surface coating layer comprises a lubricant material.

8. The surgical instrument of claim 7, wherein the second surface coating layer comprises a bone wax layer.

9. A surgical stapler comprising:
a jaw assembly comprising:
an anvil comprising a first channel formed therein, and a reload support coupled to the anvil, the reload support comprising a second channel formed therein; and
a firing member longitudinally slidably engaged with the jaw assembly to pivotably move the anvil with respect to the reload support and actuate the jaw assembly, the firing member having an I-beam profile defined by an upper flange connected to a lower flange by a vertical blade member, the upper flange being slidable within the first channel and the lower flange being slidable within the second channel;
wherein the anvil, the reload support, and the firing member each comprise sliding surfaces defined by a metallic surface layer, a first surface coating layer overlying the metallic surface layer, and a second surface coating layer overlying the first surface coating layer, and
wherein the metallic surface layer of the sliding surface of the anvil and the reload support has a first hardness, wherein the metallic surface layer of the sliding surface of the firing member has a second hardness, and wherein the second hardness is lower than the first hardness.

10. The surgical stapler of claim 9, wherein the first hardness and the second hardness are within the range of approximately 45 HRC to approximately 70 HRC.

11. The surgical stapler of claim 10, wherein the second hardness is up to approximately 10 HRC smaller than the first hardness.

12. The surgical stapler of claim 9, wherein the first surface coating layer comprises a dry film surface coating.

13. The surgical stapler of claim 9, wherein the second surface coating layer comprises a bone wax layer.

* * * * *